United States Patent
Weyl et al.

(10) Patent No.: US 6,940,287 B2
(45) Date of Patent: Sep. 6, 2005

(54) UNHEATED PLANAR SENSOR ELEMENT FOR DETERMINING THE CONCENTRATION OF A GAS COMPONENT IN A GAS MIXTURE

(75) Inventors: Helmut Weyl, Schwieberdingen (DE); Jens Schneider, La Primaube (FR); Detlef Heimann, Gerlingen (DE); Thomas Wahl, Pforzheim (DE); Hans-Joerg Renz, Leinfelden-Echterdingen (DE); Norman Hahn, Anderson, SC (US); James Richard Waldrop, II, Belton, SC (US); Damien Barnes, Anderson, SC (US); Mike McCormick, Anderson, SC (US); John Day, Greenville, SC (US)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 10/798,746

(22) Filed: Mar. 10, 2004

(65) Prior Publication Data

US 2005/0093551 A1 May 5, 2005

(30) Foreign Application Priority Data

Mar. 13, 2003 (DE) .......................... 103 10 953

(51) Int. Cl.$^7$ .......................... G01N 27/62; G01N 27/26
(52) U.S. Cl. .......................... 324/464; 204/426; 204/431
(58) Field of Search .......................... 324/464, 71.1; 73/23.31; 204/421–429, 431

(56) References Cited

U.S. PATENT DOCUMENTS 6,222,372 B1 * 4/2001 Fukaya et al. .............. 324/464

2001/0047939 A1 * 12/2001 Springhorn ................. 204/431
2003/0047452 A1 * 3/2003 Jain et al. .................... 204/421

FOREIGN PATENT DOCUMENTS

DE 199 41 051 3/2001 ................. 204/424

OTHER PUBLICATIONS

Wiedenmann, Hötzel, Neumann, Riegel, Weyl ZrO$_2$ Lambda Sensors For The Mixture Control In The Motor Vehicle, B.G. Teubner Stuttgart, 1995, pp. 383 and 384, month not available.

Chapter 6, "Exhaust Gas Sensors" of the Automotive Electronics Handbook, ¶6.3.3, date not available.

* cited by examiner

Primary Examiner—Anjan Deb
Assistant Examiner—Amy He
(74) Attorney, Agent, or Firm—Kenyon & Kenyon

(57) ABSTRACT

An unheated planar sensor element for determining the concentration of a gas component in a gas mixture, in particular the oxygen concentration in the exhaust gas of an internal combustion engine, has a sensor foil made of a solid electrolyte with an outer electrode exposed to the measuring gas, and an inner electrode exposed to a reference gas, as well as a reference-gas channel, which is covered by the sensor foil on one side and accommodates the inner electrode. To produce a small-volume, cost-effective unheated sensor element for use in small combustion engines having low power output yet sufficiently satisfactory measuring accuracy, the reference-gas channel is sealed on the underside by an additional sensor foil made of a solid electrolyte, and covered by an inner electrode lying inside the reference-gas channel and an outer electrode exposed to the measuring gas.

8 Claims, 1 Drawing Sheet

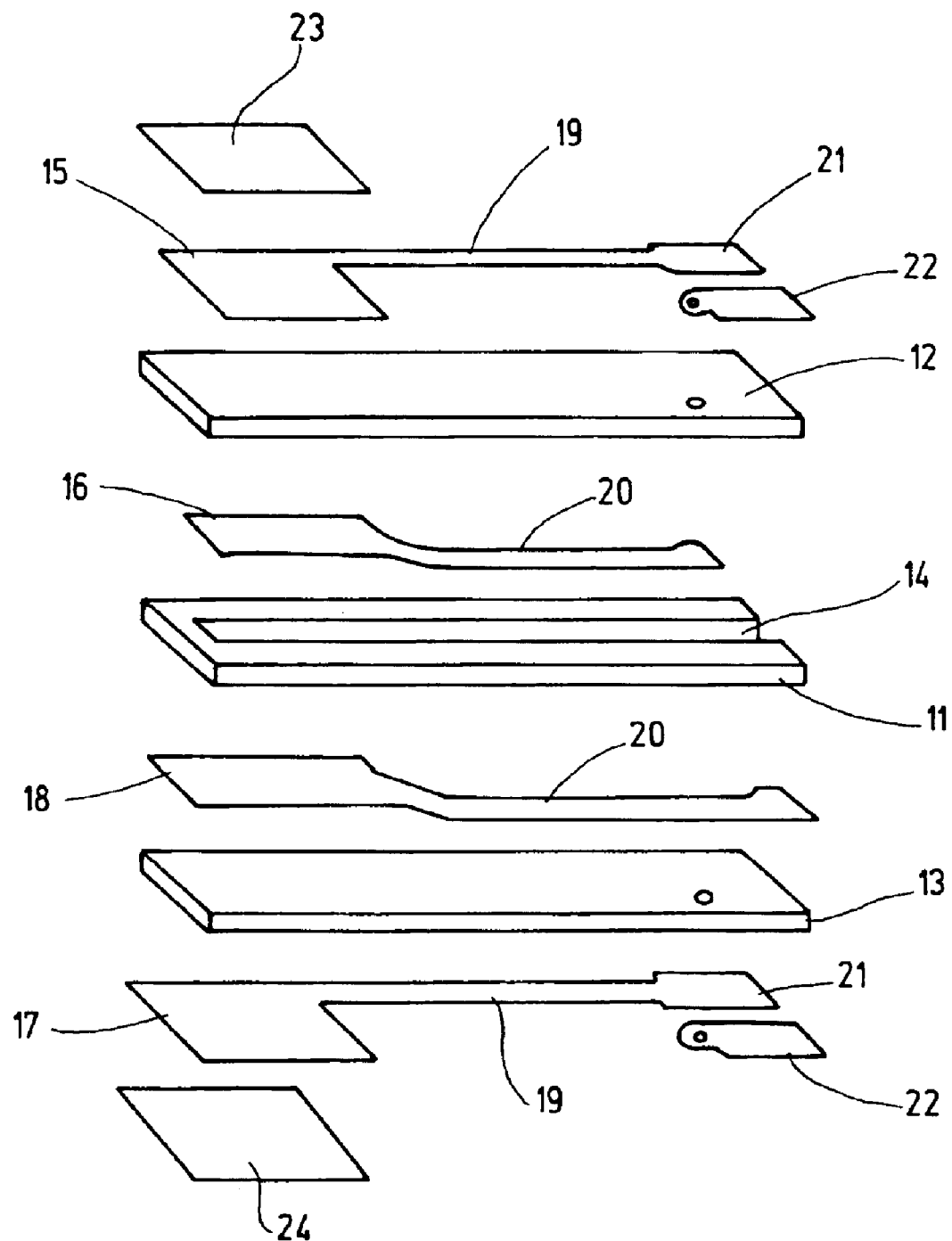

UNHEATED PLANAR SENSOR ELEMENT FOR DETERMINING THE CONCENTRATION OF A GAS COMPONENT IN A GAS MIXTURE

FIELD OF THE INVENTION

The present invention is based on an unheated planar sensor element for determining the concentration of a gas component in a gas mixture, in particular the oxygen concentration in the exhaust gas of an internal combustion engine.

BACKGROUND INFORMATION

In contrast to so-called finger sensors, planar sensor elements as they are used to determine the oxygen concentration in the exhaust gas of internal combustion engines in so-called lambda sensors, for example, are distinguished in that all functional layers, such as Nernst cell and reference-gas channel, are implemented as planar, superposed surfaces. A planar sensor element designed for a broadband lambda sensor is described in German Patent Application No. DE 199 41 051. A planar sensor element used for a jump sensor or lambda=1 sensor is to be found in "Wiedenmann, Hötzel, Neumann, Riegel, Weyl $ZrO_2$ Lambda Sensors For The Mixture Control In The Motor Vehicle, B. G. Teubner Stuttgart, 1995, pages 383 and 384".

In order to comply with higher demands regarding the precision of sensors as a result of more stringent emission standards for motor vehicles, the sensor elements are predominantly designed to include an integrated heater; unheated sensor elements, on the other hand, are no longer of great importance in the motor-vehicle sector.

SUMMARY OF THE INVENTION

The unheated planar sensor element according to the present invention has the advantage that the sensor element has a small volume due to the fact that the integrated heater is omitted, and no significant energy consumption, thus making it eminently suitable for use in small engines having low output, such as small motorcycles, lawn mowers, emergency power generators and motorized chain saws, all of which are currently offered without exhaust regulation. Thus, in these devices the exhaust composition may be considerably improved as well, in the sense of making them ecologically compatible.

The reduced measuring precision that goes hand in hand with the elimination of a heater in conventionally configured planar sensor elements is largely compensated by the layer configuration of the sensor elements according to the present invention. For, on the one hand, the inner electrodes are separated from the exhaust gas by a considerably reduced layer thickness due to the mirror-symmetrical design of the sensor element with respect to the reference-gas channel, so that the exhaust gas heats them much more rapidly and with only a slight delay with respect to the outer electrodes. On the other hand, the electrode surfaces are doubled without enlarging the longitudinal dimensions of the sensor element which are critical for the installation in a housing. Overall, it is thereby possible to realize shorter switching times in the lambda=1 regulation as well as sufficiently high control precision. It is simultaneously ensured that the two inner electrodes, on the one hand, and the two outer electrodes, on the other hand, are at the same temperature level at the same time, thereby ensuring sufficiently precise measuring accuracy.

BRIEF DESCRIPTION OF THE DRAWING

The FIGURE shows an exemplary embodiment of an unheated planar sensor element for a lambda=1 sensor in an exploded view, according to the present invention.

DETAILED DESCRIPTION

The unheated planar sensor element for determining the oxygen concentration in the exhaust gas of an internal combustion engine, shown in the FIGURE as an exemplary embodiment of a sensor element for the general determination of the concentration of a gas component in a gas mixture, has a total of three foils made of a solid electrolyte, preferably a zirconium oxide substrate ($ZrO_2$ substrate), which are positioned on top of each other and laminated together. In the following, the center foil is called channel foil 11, and the upper and lower foils are referred to as sensor foils 12 and 13. Punched out of channel foil 11 is an elongated reference-gas channel 14, which is in connection with a reference gas, generally, air. On the outer side of upper sensor foil 12, facing away from channel foil 11, is an outer electrode 15 and, lying opposite it on the inner side of sensor foil 12 facing channel foil 11, is an inner electrode 16. In the same manner, lower sensor foil 13 is covered by an outer electrode 17 and an inner electrode 18. Electrodes 15 through 18 are printed onto sensor foils 12,13 as thin platinum layers or as platinum cermet layers, using screen printing methods. Inner electrodes 16, 18 are dimensioned such that, given superposed foils 11, 12 and 13, they are situated inside reference-gas channel 14 stamped out of channel foil 11, reference-gas channel 14 being covered on top and from below by the two sensor foils 12, 13 in a gas-tight manner.

Electrodes 15, 16 are connected to contact surfaces 21, 22 via printed circuit traces 19, 20, which are likewise printed onto sensor foils 12, 13. In each sensor foil 12 and 13, the two contact surfaces 21, 22 are applied onto the outer side of sensor foil 12 and 13, respectively, while printed circuit trace 19 is applied onto the outer side and printed circuit trace 20 onto the inner side of sensor foils 12 and 13, respectively. Contact surface 21 merges without transition with printed circuit 19, contact surface 22, through sensor foils 12 and 13, being contacted onto (connected to) printed circuit trace 20, to inner electrode 17 and 18, respectively. The sensor element, accommodated in a housing, is connected to a control device via contact surfaces 21, 22 by means of connecting cables guided through the housing. Outer electrodes 15 and 17 are each coated by a porous, adhesive protective layer 23 and 24, respectively, which are likewise printed using screen-printing methods. The protective layers consist of magnesium spinel, for example, or of $Y_2O_3$-, MgO- or CaO-stabilizing $ZrO_2$. Pore forming material that burns out during sintering or $Al_2O_3$ are admixed to adjust a defined porosity.

In a modification of the described sensor element, it is dispensed with channel foil 11 having punched out reference-gas channel 14. To form reference-gas channel 14, the reference-gas channel is applied as porous layer onto the inner sides of sensor foil 12 or sensor foil 13, using the same layout as the punched out channel. In addition, a u-shaped, gas-tight $ZrO_2$ layer is overprinted, which seals the reference-gas channel from the outside and includes a cutout for access to the reference gas. The application is implemented by means of screen printing methods using thick-film or thin-film technology. After placing sensor foils 12, 13 on top of one another and laminating the sensor foils together, reference-gas channel 14 is covered again on the top and bottom by the two sensor foils 12, 13, and inner electrodes 16, 18 printed onto the underside of sensor foils 12, 13 are situated inside reference-gas channel 14. In this modification of the sensor element, a foil is dispensed with, to be replaced by a fairly thin printed layer. This allows the height or thickness of the sensor element to be reduced.

The present invention is not restricted to a sensor element for determining the oxygen concentration in the exhaust gas. For example, any sensor elements that are to be used to determine the concentration of any gas component in a gas mixture, for instance to determine the concentration of nitrogen oxides in the exhaust gas, may be configured in the manner described.

What is claimed is:

1. An unheated planar sensor element for determining a concentration of a gas component in a gas mixture, comprising:

a first sensor foil composed of a solid electrolyte;

a reference-gas channel;

a first outer electrode situated on an outer side of the first sensor foil, the first outer electrode being exposed to the gas mixture;

a first inner electrode situated on an inner side of the first sensor foil, the first inner electrode being exposed to a reference gas, the first inner electrode being situated inside the reference-gas channel covered on top by the first sensor foil;

a second sensor foil covering an underside of the reference-gas channel, the second sensor foil being composed of a solid electrolyte;

a second inner electrode situated on an inner side of the second sensor foil, the second inner electrode being situated inside the reference-gas channel; and a second outer electrode situated on an outer side of the second sensor foil, the second outer electrode being exposed to the gas mixture.

2. The sensor element according to claim 1, wherein the sensor element is for determining an oxygen concentration in an exhaust gas of an internal combustion engine.

3. The sensor element according to claim 1, further comprising a foil, and wherein the reference-gas channel is punched out of the foil, the foil being embedded between the first and second sensor foils.

4. The sensor element according to claim 3, wherein the foil having the punched-out reference-gas channel is composed of a solid electrolyte.

5. The sensor element according to claim 1, wherein onto one of the first and second sensor foils the reference-gas channel is applied as a porous layer, and a u-shaped layer composed of a solid electrolyte, which seals the reference-gas channel from the outside.

6. The sensor element according to claim 5, wherein the u-shaped layer is composed of $ZrO_2$.

7. The sensor element according to claim 5, wherein an application of the reference-gas channel and the u-shaped solid-electrolyte layer is implemented using screen-printing methods.

8. The sensor element according to claim 1, further comprising a gas permeable, porous protective layer situated on an upper surface, facing away from the first sensor foil, of each of the first and second outer electrodes.

* * * * *